(12) United States Patent
Kuppens et al.

(10) Patent No.: US 12,067,719 B2
(45) Date of Patent: Aug. 20, 2024

(54) DETERMINING REGION(S) FOR TISSUE DISSECTION IN PATHOLOGY SLIDES

(71) Applicant: XYALL B.V., Eindhoven (NL)

(72) Inventors: Henricus Rudolphus Kuppens, Nuenen (NL); Evgenia Balmashnova, Eindhoven (NL); Hans Van Wijngaarden, 's-Hertogenbosch (NL)

(73) Assignee: Xayall B.V., Eindhoven (NL)

( * ) Notice: Subject to any disclaimer, the term of this patent is extended or adjusted under 35 U.S.C. 154(b) by 487 days.

(21) Appl. No.: 17/624,501

(22) PCT Filed: Jul. 3, 2020

(86) PCT No.: PCT/EP2020/068907
§ 371 (c)(1),
(2) Date: Jan. 3, 2022

(87) PCT Pub. No.: WO2021/001564
PCT Pub. Date: Jan. 7, 2021

(65) Prior Publication Data
US 2022/0375070 A1    Nov. 24, 2022

(30) Foreign Application Priority Data

Jul. 3, 2019    (EP) .................................... 19184236

(51) Int. Cl.
*G06T 7/00*    (2017.01)
*G01N 1/30*    (2006.01)
(Continued)

(52) U.S. Cl.
CPC ............. *G06T 7/0012* (2013.01); *G01N 1/30* (2013.01); *G06T 7/33* (2017.01); *G06V 10/46* (2022.01); *G06T 2207/30024* (2013.01)

(58) Field of Classification Search
CPC ..................... G06T 7/0012; G06T 7/33; G06T 2207/30024; G06T 7/30;
(Continued)

(56) References Cited

U.S. PATENT DOCUMENTS 10,503,868 B2 *   12/2019   Chukka ...................... G06T 7/33
11,125,660 B2 *   9/2021    Barnes .................. G06T 7/0014
(Continued)

FOREIGN PATENT DOCUMENTS

EP           3245069 B1       9/2018
JP        2012208234 A      10/2012
(Continued)

OTHER PUBLICATIONS

Mar. 5, 2024 Japanese Office Action.
(Continued)

*Primary Examiner* — Juan A Torres
(74) *Attorney, Agent, or Firm* — Whitestone Law, PLLC

(57) ABSTRACT

Some embodiments are directed to a system and computer-implemented method are provided for determining one or more regions for tissue dissection in a series of pathology slides using a series of images which represent a digitized version of the series of pathology slides. Annotations are obtained for at least two reference images, with each annotation representing a region for tissue dissection in the respective reference image. Annotations are then generated for intermediate images between the reference images on the basis of bidirectional image registration and the subsequent propagation of both annotations to each intermediate image, which annotations are then combined to obtain a combined annotation for each intermediate image. The above measures are well suited to generate annotations for series of pathology slides which contain tissue slices of a tissue of interest having a complex 3D shape.

15 Claims, 6 Drawing Sheets

(51) Int. Cl.
*G06T 7/33* (2017.01)
*G06V 10/46* (2022.01)

(58) Field of Classification Search
CPC ......... G06T 2207/20128; G06T 7/0014; G06T 2207/10056; G01N 1/30; G06V 10/46; G06V 20/698; G16H 30/40; G16H 50/20
USPC .......................................................... 382/128
See application file for complete search history.

(56) References Cited

U.S. PATENT DOCUMENTS

| | | |
|---|---|---|
| 2006/0134600 A1 | 6/2006 | Fuhr et al. |
| 2012/0045790 A1 | 2/2012 | Van Dijk et al. |
| 2012/0069049 A1* | 3/2012 | Howe ................ G06V 20/693 345/629 |
| 2012/0076390 A1 | 3/2012 | Potts et al. |
| 2012/0257811 A1 | 10/2012 | Metzger et al. |
| 2015/0262329 A1 | 9/2015 | Vink et al. |
| 2016/0131559 A1 | 5/2016 | Wimberger-Friedl et al. |
| 2017/0116734 A1 | 4/2017 | Van Leeuwen et al. |
| 2017/0270666 A1* | 9/2017 | Barnes ............. G01N 33/57415 |
| 2018/0137689 A1 | 5/2018 | Eastwood et al. |
| 2018/0225872 A1 | 8/2018 | Vink et al. |
| 2018/0267290 A1 | 9/2018 | Boamfa et al. |

FOREIGN PATENT DOCUMENTS

| | | |
|---|---|---|
| WO | WO2008/080403 A1 | 7/2008 |
| WO | 2012102779 A2 | 8/2012 |
| WO | WO2014/140070 A2 | 9/2014 |
| WO | WO2015/018750 A1 | 2/2015 |
| WO | 2016009862 A1 | 1/2016 |
| WO | WO2016/087592 A1 | 6/2016 |
| WO | WO2016/120433 A1 | 8/2016 |
| WO | WO2016/120434 A1 | 8/2016 |
| WO | WO2017/009337 A1 | 1/2017 |
| WO | WO2018/229052 A1 | 12/2018 |

OTHER PUBLICATIONS

International Search Report and Written Opinion for PCT Patent App. No. PCT/EP2020/068907 (Oct. 14, 2020).

Doche, M. E., et al., "Data Integration from Pathology Slides for Quantitative Imaging of Multiple Cell Types Within the Tumor Immune Cell Infiltrate," Diagnostic. Path. 2017;12:17 pp.

Campbell, W. S., et al., "Application of whole slide image markup and annotation for pathologist knowledge capture," J. Pathol. Inform. 2013;4:14 pp.

* cited by examiner

_US 12,067,719 B2_

DETERMINING REGION(S) FOR TISSUE DISSECTION IN PATHOLOGY SLIDES

CROSS REFERENCE TO RELATED APPLICATIONS

This application is a national phase filing under 35 C.F.R. § 371 of and claims priority to PCT Patent Application No. PCT/EP2020/068907, filed on Jul. 3, 2020, which claims the priority benefit under 35 U.S.C. § 119 of European Patent Application No. 19184236.8 filed on Jul. 3, 2019, the contents of each of which are hereby incorporated in their entireties by reference.

BACKGROUND

Some embodiments of the presently disclosed subject matter relate to pathology and digital pathology, and in particular to a system and computer-implemented method for determining one or more regions for tissue dissection in a series of pathology slides. Some other embodiments of the presently disclosed subject matter relate to controlling a tissue dissection system based on one or more annotations generated by the system or the method. Some other embodiments of the presently disclosed subject matter relate to computer-readable medium including instructions for causing a processor system to perform the computer-implemented method.

In the field of pathology, a surgeon may often remove a sample of tissue from a patient for examination by the hospital's pathology department or elsewhere. This tissue sample may be embedded in paraffin to form what is typically referred to as a 'tissue block'. A pathologist may slice the tissue block into very thin layers that are placed on glass slides and examined under a microscope. This may allow the pathologist to establish a diagnosis.

There exist various specific uses of pathology. For example, pathology may be used in guiding the treatment decision for individual patients with cancer, e.g., using so-called genomic-based diagnostic tests. This may involve isolating cancer cells in tissue which is commonly prepared on glass slides, and using the isolated cancer cells in a Polymerase Chain Reaction (PCR) process to 'amplify' the DNA and or RNA and thereby enable specific genetic aberrations of interest to be detected or quantified.

Commonly known methods for isolating cancer cells from surrounding non-cancer cells, or in general for isolating tissue of interest from surrounding tissue, include but are not limited to manual dissection, e.g., by cutting and/or lifting tissue using a razor blade and (semi)automatic dissection using a milling tool, a laser, resolving fluid and the like.

The regions in which tissue is to be dissected may be determined using techniques from digital pathology. Such digital pathology is based on the digitization of pathology slides, referring to the conversion of tissue slices placed on glass slides into digital images ('digital slides') that can be viewed, managed, shared and analyzed on a display, such as a computer monitor. A pathologist may thereby specify regions for tissue extraction by digitally annotating images, e.g., using a mouse, pen or touch screen. For example, a pathologist may indicate such regions by selecting and placing geometrical primitives in the image, e.g., lines, circles, rectangles or other types of polygons, which may then be adjusted in size and/or shape. Additionally or alternatively, a pathologist may define such geometrical primitives, e.g., by a so-called 'freeform' tool, or may simply freely draw in the image, etc. It is also known to automatically or semi-automatically annotate morphological structures in an image. Such techniques may be used to automatically or semi-automatically determine regions for tissue extraction if such regions are linked to a morphological structure.

Normally, a region for tissue dissection is annotated in images in which the tissue is stained using a staining agent to increase the visibility of certain types of biological material, which may in turn facilitate the identification of the tissue of interest, being for example cancer cells. For example, Hematoxylin and Eosin (H&E) may be applied to tissue to obtain stained 'reference' slides in which the tissue of interest is better identifiable. At the same time, it may be possible to dissect the tissue of interest from unstained slides, these also being referred to as 'extraction' slides. There may thus be a need to transfer an annotation representing a region for tissue dissection from a stained reference slide to an unstained extraction slide, or in general from one image to another image.

US20180267290A1 describes a method for selecting a sample removing area of an unstained sample to be removed for molecular diagnosis. The method includes the following steps: a) selecting a reference removing area in a reference image of a reference slice of an object, wherein biological material in the reference slice is stained, b) obtaining a digital sample image of a sample slice of the object under an imaging setting, wherein the biological material in the sample slice is unstained, c) registering the digital sample image with the reference image for translating the reference removing area in the reference image to the digital sample image, and d) identifying a sample removing area in the digital sample image based on the translated reference removing area.

Disadvantageously, US20180267290A1 is insufficiently robust in case the biological material has a different shape and/or position across the slices.

SUMMARY

Accordingly, some embodiments of the presently disclosed subject matter are directed to more robustly transfer annotations which identify regions for tissue dissection from reference images to one or more extraction images.

In accordance with some embodiments of the presently disclosed subject matter, a computer-implemented method is provided for determining one or more regions for tissue dissection in a series of pathology slides using a series of images which represent a digitized version of the series of pathology slides. The method includes:

- obtaining a first annotation identifying a first region for tissue dissection in a first image of the series of images;
- obtaining a second annotation identifying a second region for tissue dissection in a second image of the series of images, wherein the first image and the second image are separated in the series of images by a series of intermediate images; and
- generating an annotation for one or more intermediate images from the series of intermediate images by, for each one of the one or more images:
  - determining a first set of registration parameters representing an at least partial registration of the intermediate image with the first image;
  - determining a second set of registration parameters representing an at least partial registration of the intermediate image with the second image;

propagating the first annotation from the first image to the intermediate image using the first set of registration parameters;

propagating the second annotation from the second image to the intermediate image using the second set of registration parameters; and combining the propagated first annotation and second annotation to obtain the annotation in the intermediate image.

In accordance with a some other embodiments of the presently disclosed subject matter, a system is provided for determining one or more regions for tissue dissection in a series of pathology slides using a series of images which represent a digitized version of the series of pathology slides.

The system includes:
a data interface for accessing the series of images;
a further data interface for accessing annotation input data defining:
  a first annotation identifying a first region for tissue dissection in a first image of the series of images, and
  a second annotation identifying a second region for tissue dissection in a second image of the series of images, wherein the first image and the second image are separated in the series of images by a series of intermediate images; and
a processor subsystem configured to:
  generate an annotation for one or more intermediate images from the series of intermediate images by, for each one of the one or more images:
    determining a first set of registration parameters representing an at least partial registration of the intermediate image with the first image;
    determining a second set of registration parameters representing an at least partial registration of the intermediate image with the second image;
    propagating the first annotation from the first image to the intermediate image using the first set of registration parameters;
    propagating the second annotation from the second image to the intermediate image using the second set of registration parameters; and
    combining the propagated first annotation and second annotation to obtain the annotation in the intermediate image.

In accordance with some other embodiments of the presently disclosed subject matter, a computer-readable medium is provided including transitory or non-transitory data representing instructions arranged to cause a processor system to perform the computer-implemented method.

The above measures are based on the insight that the shape and position of tissue of interest may vary greatly across a series of pathology slides, and thereby also across a series of images which represent a digitized version of the series of pathology slides. For example, a tumor may have a complex and irregular 3D shape, and the 2D intersections of this 3D shape may vary greatly from one pathology slide to the next. Tissue of interest may also have a complex shape, such as in the case of prostate biopsy.

Accordingly, in case an annotation of a region for tissue dissection is obtained for one of the images, e.g., a 'reference' image, it may be difficult to transfer this annotation to other 'extraction' images. Here, the reference image may correspond to an H&E stained pathology slide or may in any other manner represent an image which facilitates the annotation of the region for tissue extraction, while the extraction images may correspond to unstained pathology slides, to Nuclear Fast Red (NFR) stained pathology slides or may in any other manner represent images for which an annotation of the region for tissue extraction may be unavailable or more difficult to obtain than for a reference image.

The above measures involve obtaining annotations which identify respective regions for tissue dissection in at least two reference images. Both reference images are separated in the series of images by a series of intermediate images which represent the digitized versions of a series of intermediate pathology slides. The annotation may have been obtained in a manner as known per se, e.g., by manual annotation by a pathologist, or in some embodiments by semi-automatic or automatic annotation.

An annotation for at least one of the intermediate images may be obtained by at least in part registering each reference image with the intermediate image. Such registration is known per se, and typically expresses correspondences between the image content of images, and is thereby also referred to as 'image registration'. Here, the term 'at least in part' refers to at least part of the reference image being registered with the intermediate image, e.g., a spatial sub-region, or select image features, etc. Each registration may be defined by a set of parameters, as is known per se. For example, the registration may be a parametric registration, but may also include registrations which are conventionally considered as non-parametric registrations, e.g., being defined by a deformation field or the like. In the latter example, the registration parameters may define deformation vectors.

Having obtained both annotations, each annotation may be transferred to the intermediate image on the basis of the respective registration. Such transfer may typically involve deforming the annotation in accordance with the registration. For example, if an elastic registration is used, the elastic registration may indicate a deformation of image content, which may be applied in a likewise manner to the annotation overlaying the image content. Accordingly, two annotations may be obtained for the intermediate image, which may then be combined into one, for example using morphological operations, for example taking into account an overlap in shape, or a distance transform or a shape context, etc.

Compared to known techniques for transferring an annotation from a reference image to an extraction image, the above measures transfer two or more annotations obtained for respective reference images at both sides of the intermediate image in the series of images. As such, the annotations may be transferred from either side of the intermediate image. The combined annotation may thus effectively represent a bidirectional interpolation of such annotations, rather than a mere extrapolation from one side. Such interpolation is better able to account for the shape and/or position of tissue of interest varying greatly across a series of pathology slides. In particular, if the shape and/or position of the tissue of interest varies greatly, both annotations may also have a different shape and/or position, e.g., by a pathologist annotating each of the reference images differently to account for the different shape and/or position. This represents additional information which may be taken into account when combining both annotations. For example, the combined annotation may only include or can consist of the overlap between both annotations, e.g., represent a logical 'AND', and thereby represent a 'conservative' annotation which is more likely to contain only the tissue of interest, compared to either annotation alone. Accordingly, a more robust annotation may be obtained compared to extrapolating an annotation from one side.

Optionally, the first set of registration parameters and the second set of registration parameters each define a deformable registration, and propagating the first annotation to the intermediate image and propagating the second annotation to the intermediate image each include deforming the respective annotation based on the respective set of registration parameters. Such deformable registration is also known as elastic registration, and typically expresses correspondences between the image content of images not only in terms of a translation and/or rotation, e.g., as an affine transformation, but also in terms of a local deformation, e.g., a non-rigid transformation. Having obtained such elastic registration parameters, both annotations may be deformed in accordance with the deformation having been calculated for the underlying image content. Thereby, each deformed annotation may better match the image content in the intermediate image.

Optionally, the method further includes determining a quality of fit of the annotation in the intermediate image, and if the quality of fit does not satisfy a quality of fit criterion, alerting a user to provide a third annotation in a third image which is included in the series of intermediate images between the first image and the second image. Such a quality of fit may be determined in various ways, for example by comparing the combined annotation to the image content in the intermediate image, and/or by comparing both propagated annotations. If the quality of fit is deemed insufficient, this may denote that the shape and/or position of the tissue of interest varies too much between each or both of the reference images and the extraction image, causing the propagation of either or both annotations to be insufficiently accurate. Accordingly, it may be desired to obtain an annotation for a nearer image, e.g., in-between both reference images, which is likely to be more similar, in terms of shape and/or position of the tissue of interest, to the intermediate image. Accordingly, the user may be alerted, e.g., using an onscreen warning or in any other way, to provide a third annotation in a third image which is included in the series of intermediate images between the first image and the second image. In some embodiments, this may involve the corresponding pathology slide having to be stained and re-digitized, thereby effectively converting an extraction slide into a reference slide, and after re-digitization, obtaining another reference image between the two original reference images.

In some embodiments, the second annotation in the second image may only need to be obtained if a quality of fit which is obtained by propagating the first annotation to the intermediate image does not satisfy a quality of fit criterion. For example, the method and system may first obtain the first annotation, determine the first set of registration parameters, propagate the first annotation from the first image to the intermediate image using the first set of registration parameters and determine the quality of fit of the resulting propagated annotation, which may in these embodiments for example be determined on the basis of user input received from a user and which user input may be indicative of the quality of fit. If the quality of fit is deemed insufficient, e.g., by not satisfying a quality of fit criterion, the method and system may obtain the second annotation, for example by alerting a user to provide the second annotation in the second image. Having obtained the second annotation, the method and system may determine the second set of registration parameters, propagate the second annotation from the second image to the intermediate image using the second set of registration parameters, and combine the propagated first annotation and second annotation to obtain the annotation in the intermediate image. In other words, the functionality relating to the second annotation and the combining of the first and the second annotation may be conditional functionality, in that the functionality may only (need to) be invoked if propagation of a single annotation yields an insufficient quality of fit.

Optionally, alerting the user includes indicating a location of the third image within the series of intermediate images or a location of a corresponding pathology slide within the series of pathology slides. For example, the user may be alerted to annotate a third image substantially in the middle of the series of intermediate images, or in other words, substantially halfway between the first image and the second image in the series of images, and thus in the middle of the corresponding series of intermediate pathology slides.

Optionally, determining the quality of fit of the annotation in the intermediate image includes determining a first quality of fit of the propagated first annotation and a second quality of fit of the propagated second annotation, and the method further includes determining the location of the third image based on a comparison of the first quality of fit and the second quality of fit. The location of the third image to be annotated may be adaptively determined based on the respective quality of fit. For example, if one of the propagated annotations yields a poor quality of fit compared to the other propagated annotation, this may indicate that the shape and/or position of the tissue of interest varies too much between the intermediate image and the corresponding reference image, and as such, it may be desired to obtain an annotation nearer to the intermediate image at the side of the intermediate image. Thereby, the annotation for the third image may replace that of the earlier reference image when generating the annotation for the intermediate image.

Optionally,
the first image and the third image are separated in the series of images by a first subseries of intermediate images;
the second image and the third image are separated in the series of images by a second subseries of intermediate images; and
wherein the method further includes:
generating an annotation for one or more intermediate images of the first subseries of intermediate images based on the first annotation and the third annotation; and
generating an annotation for one or more intermediate images of the second subseries of intermediate images based on the second annotation and the third annotation.

The above measures provide an iterative process in which, if for a particular intermediate image the quality of fit of the combined propagated annotations is deemed to be insufficient, an annotation is obtained for a third image in between the first image and the second image, after which the annotation-by-propagation process is repeated for the both sub-series individually. This iteration may be repeated until all or a sufficient number of extraction images have been annotated, after which the iterative process may cease. Advantageously, the iterative process is adaptive, in that a user may only be requested to annotate a further image (which may involve staining the corresponding pathology slide and re-digitizing the stained slide) if the quality of fit is deemed to be insufficient. Otherwise and elsewhere, the iterative process proceeds based on annotation-by-propagation.

Optionally, determining the quality of fit includes determining a difference in shape, or overlap in surface area, of the propagated first annotation and the propagated second annotation. This quality of fit measure may be used in addition, or as an alternative to a quality of fit which is based on comparing the annotation to the image content, and is based on the consideration that the propagated annotations may be considered reliable if both annotations are similar or substantially identical in terms of shape and/or size.

Optionally, determining the quality of fit includes determining a magnitude of a deformation of the propagated first annotation and/or of the propagated second annotation. A larger deformation may indicate a larger difference in shape of the tissue of interest between the respective reference image and the intermediate image, and thereby a larger likelihood that the propagated annotation insufficiently fits the intermediate image.

Optionally, determining the quality of fit is based on i) similarities and/or differences between the image data underlying the first annotation in the first image and the image data underlying the propagated first annotation in the intermediate image, and/or ii) similarities and/or differences between the image data underlying the second annotation in the second image and the image data underlying the propagated second annotation in the intermediate image. Such an image-based quality of fit may express a reliability and/or accuracy of the respective registrations, and may also be combined with the above-mentioned quality of fit based on the difference in shape or overlap in surface area. It will be appreciated that alternatively, any other known measure of the reliability and/or accuracy of the respective registrations may be used to determine the quality of fit.

Optionally, the first set of registration parameters and the second set of registration parameters are determined by one of the group of: feature-based image registration, image registration using an active contour model, image registration using shape context, and image registration using the level set method. These registration techniques are known per se and have been found to be well-suited not only for image registration, but also to propagate annotations to the one or more intermediate images.

Optionally, the first image and the second image and the third image are of Hematoxylin and Eosin (H&E) stained pathology slides, or of pathology slides stained using another staining agent which is removable or non-removable from the pathology slides.

Optionally, the series of intermediate images are of pathology slides which are unstained in paraffin, unstained without paraffin and/or stained with Nuclear Fast Red (NFR) or another staining agent which is removable from the pathology slides.

Optionally, the method further includes controlling a tissue dissection system to dissect tissue from one or more pathology slides which correspond to the one or more intermediate images based on the one or more annotations generated for the one or more intermediate images. Accordingly, the generated annotations may be used to automatically or semi-automatically extract tissue from corresponding pathology extraction slides.

Optionally, determining the first set of registration parameters includes determining individual registrations between respective image pairs in the series of images, wherein the individual registrations together form a chain of registrations between the first image and the intermediate image. As such, instead of directly determining the registration parameters between the first image and the intermediate image, the registration between the first image and the intermediate image may be obtained as a superposition of the individual registrations between the image pairs in between both images. Such registrations between image pairs (for example consecutive image pairs, or image pairs which are formed by every second or third image in the series of images) may be more robust as the distance between the images may be smaller than the distance between the first image and the intermediate image and therefore the similarity between the pair of images is expected to be higher than the similarity between the first image and the intermediate image, which may lead to a more robust overall registration. The above described 'chain-based' approach to registration may also be used to determine the second set of registration parameters, mutatis mutandis.

Optionally, the system further includes a user interface subsystem including:
 a display output for displaying respective images on a display;
 a user input interface for receiving user input data from a user input device operable by a user;
 wherein the processor subsystem is configured to, via the user interface subsystem, enable a user to provide the first annotation identifying the first region for tissue dissection in the first image and to provide the second annotation identifying the second region for tissue dissection in the second image of the series of images.

The system may thus be configured to enable a user to manually define the first annotation and the second annotation. In such embodiments, the aforementioned annotation input data may be data which may be generated by the processor subsystem as a result of the annotation by the user. In such embodiments, the further data interface may be an internal data interface of the processor subsystem, such as a memory interface.

Optionally, the system is configured to generate the annotation input data by applying an annotation technique to the first image and to the second image to obtain the first annotation and the second annotation. The annotation technique may be a known type of automatic annotation technique, but also a semi-automatic annotation technique for which the user may provide additional user input via the aforementioned user interface subsystem.

Optionally, the system is part of or configured to interface with a tissue dissection system.

It will be appreciated by those of ordinary skill in the art that two or more of the above-mentioned embodiments, implementations, and/or some optional embodiments of the presently disclosed subject matter may be combined in any way deemed useful.

Modifications and variations of any computer-implemented method and/or any computer program product, which correspond to the described modifications and variations of a corresponding system, can be carried out by a person of ordinary skill in the art on the basis of the present description, and vice versa.

BRIEF DESCRIPTION OF THE DRAWINGS

These and other embodiments of the presently disclosed subject matter are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

LIST OF REFERENCE NUMBERS

The following list of reference numbers is provided for facilitating the interpretation of the drawings and shall not be construed as limiting the claims.

| | |
|---|---|
| 10, 11 | tissue block |
| 15 | cutting |
| 20, 21 | tissue material |
| 30-86 | pathology slides (* = containing H&E stained tissue) |
| 90-95 | registration between pairs of images |
| 100-107 | tissue part (not H&E stained) |
| 150, 151 | tissue part (H&E stained) |
| 200-203 | annotation representing region for tissue dissection |
| 250-254 | transferred annotation |
| 300 | system for determining tissue dissection regions |
| 320 | data interface |
| 340 | processor subsystem |
| 342, 344 | internal data communication |
| 360 | user interface subsystem |
| 370 | display output |
| 380 | user input interface |
| 400 | data storage |
| 410 | image data |
| 412 | annotation output data |
| 420 | display |
| 422 | display data |
| 440 | user input device |
| 442 | user input data |
| 500 | method for determining tissue dissection regions |
| 510 | obtaining first annotation in first image |
| 520 | obtaining second annotation in second image |
| 530 | generating annotation for intermediate image(s) |
| 540 | determining first set of registration parameters |
| 550 | determining second set of registration parameters |
| 560 | propagating first annotation to intermediate image |
| 570 | propagating second annotation to intermediate image |
| 580 | combining propagated first annotation and second annotation |
| 600 | computer readable medium |
| 610 | instruction data |

DETAILED DESCRIPTION OF EXEMPLARY EMBODIMENTS

Figure 1:
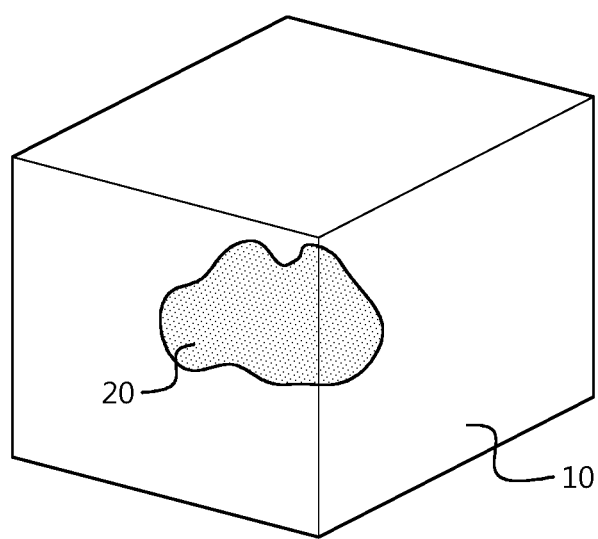
FIG. 1 shows tissue material which is embedded in a block of paraffin to form a tissue block.
Figure 2:
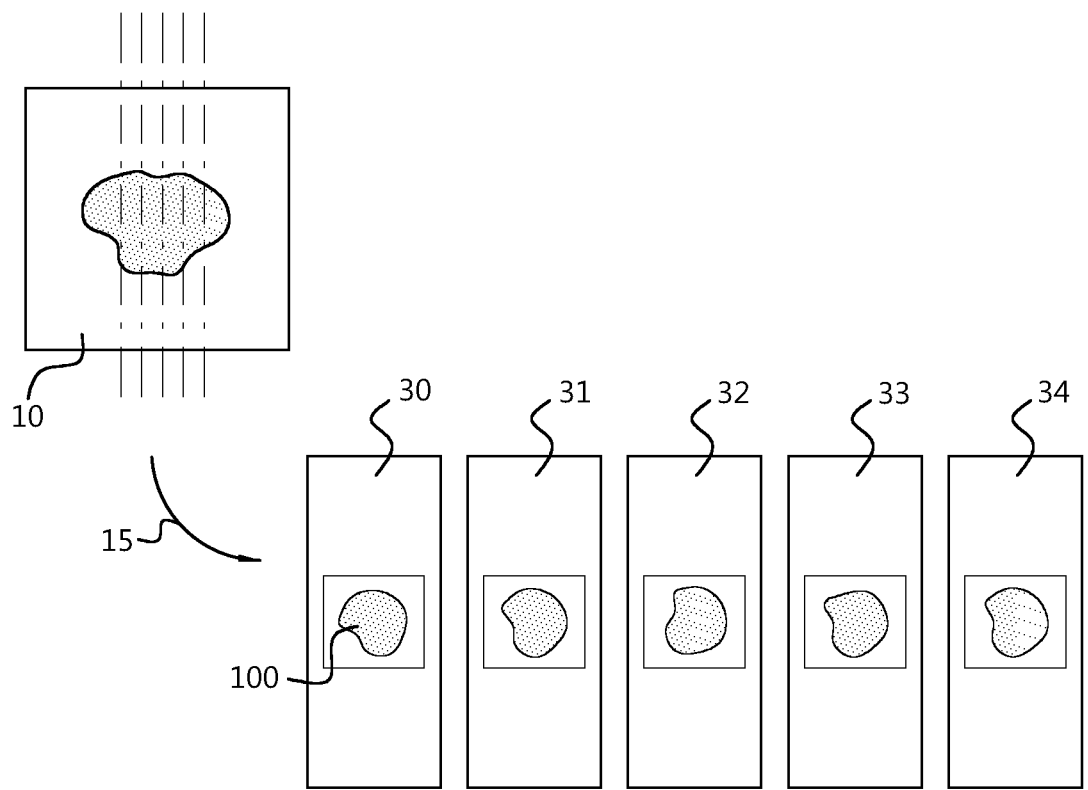
FIG. 2 illustrates the slicing of the tissue block to obtain a series of pathology slides, in which each pathology slide contains a respective tissue part.

FIG. 1 shows a tissue block 10 which contains tissue material 20 which may be removed from a patient during surgery or biopsy or the like, and which may contain diseased tissue, for example a lesion, or any other type of tissue of interest. To obtain the tissue block 10, the tissue material 20 may be impregnated with and embedded in paraffin. To enable the pathological or histological examination of the tissue of interest, the tissue block may be sliced and the resulting one or more tissue slices may each be transferred onto separate glass slides, which enables examination by optical microscope but also their digitization, e.g., by a so-called digital slide scanner which are known in per se from the field of digital pathology. FIG. 2 illustrates this slicing of the tissue block 10 and the mounting of the resulting tissue slices onto glass slides (both indicated by arrow 15 in FIG. 2) and the result thereof, namely a series of pathology slides 30-34. In FIG. 2, each slice in the series of pathology slides 30-34 is shown to include a tissue part 100.

Figure 3:
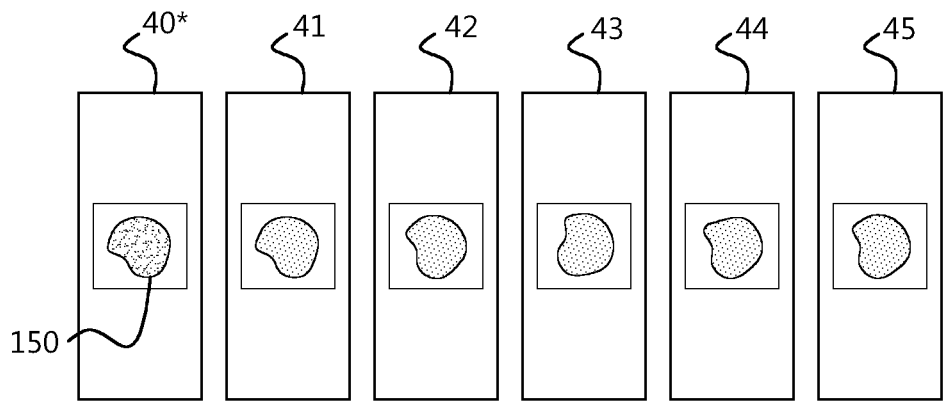
FIG. 3 illustrates a series of pathology slides in which the tissue in one pathology slide is stained by H&E and the remaining pathology slides are not stained by H&E.

FIG. 3 illustrates a series of pathology slides 40*-45 in which the tissue in a first pathology slide 40* is stained by Hematoxylin and Eosin (H&E). Such type of staining is well known in the field of pathology and histology, and may be applied to increase the visibility of certain type of biological material, which in turn may facilitate the identification of certain tissue of interest, being for example the tissue part 150, or a part of the tissue part 150.

FIG. 3 shows the remaining pathology slides 41-45 not being stained by H&E. In general, a series of pathology slides may contain a H&E stained pathology slide, being also referred to as a 'reference slide' for reasons as described further onwards, and one or more pathology slides which are unstained or stained with Nuclear Fast Red (NFR) or a similar staining agent which does not affect the Polymerase Chain Reaction (PCR) process and/or which is removable before PCR. A pathology slide containing H&E stained tissue is here and elsewhere also simply referred to as a 'stained pathology slide' and marked with a reference numeral followed by an asterix. The pathology slides containing unstained (in or without paraffin) or NFR stained tissue may be used in the tissue dissection, this also being referred to as tissue extraction and the corresponding slides being referred to as 'extraction slides'.

Figure 4:
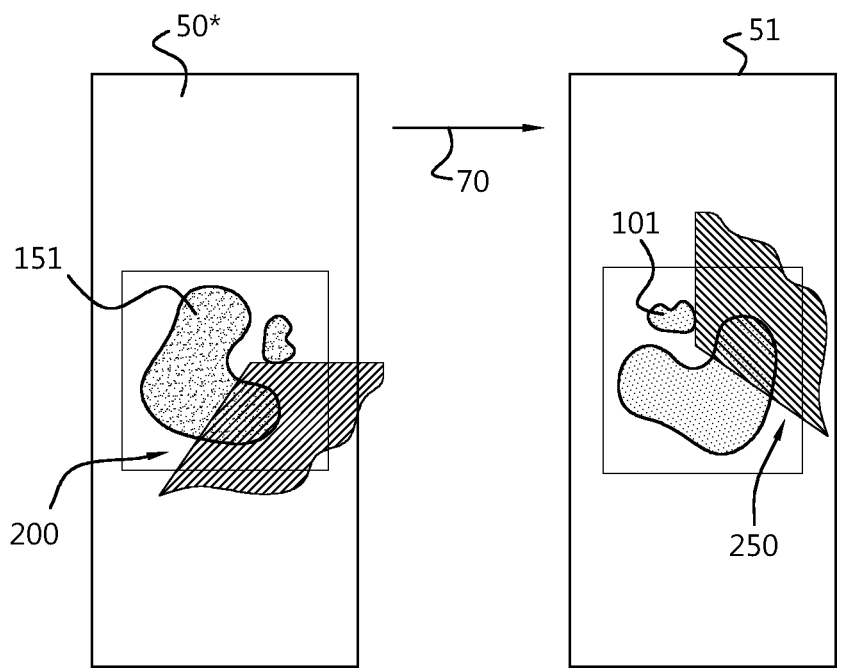
FIG. 4 illustrates the annotation of the H&E stained pathology slide and the transfer of the annotation to a pathology slide which is not stained by H&E.

FIG. 4 illustrates the annotation of a H&E stained pathology slide 50*. Such an annotation 200 may be performed on the physical slide 50* itself, e.g., using a marker, but is normally nowadays applied to a digitized version of the pathology slide, e.g., to an image thereof. As such, any reference to an annotation being applied (or generated, transferred, etc.) to a pathology slide is to be understood as including the annotation being applied (or generated, transferred, etc.) digitally to a digitized version of the pathology slide. Such digital annotation is known per se, and may be performed by a user, such as a pathologist, by operating a digital pathology software package, or by a (semi)automatic algorithm. It is further noted that such digital annotations are in principle also obtainable by physically marking the pathology slide and by digitizing the pathology slide with its annotation.

In general, the annotation 200 may be applied to mark a tissue of interest, and in many cases, to specifically mark a region for tissue dissection. As illustrated in FIG. 4, the shape of the annotation 200 does not need to correspond to the shape of the anatomical structure, e.g., the tissue part 151 which is or contains the tissue of interest, but may do so. For example, the annotation 200 may include a part of the surrounding paraffin, or may extend beyond the paraffin or may extend into an area which previously contained paraffin but which has been removed before digitizing the tissue slices.

It may be possible not to perform the tissue extraction on the reference slide 50* due to the H&E staining, but rather on one of the extraction slides. Therefore, as indicated by the arrow 70 in FIG. 4, the annotation 200 may be transferred from the reference slide 50* to an extraction slide 51 to obtain an annotation 250 in the extraction slide 51. It is known to transfer such an annotation by translating a digital annotation based on image registration between the corresponding images of both slides. Namely, since the image registration may determine correspondences between the image data of the reference slide 50* and that of the extraction slide 51, and thereby correspondences between the tissue part 151 and the tissue part 101, the annotation 200 may be translated in accordance with the correspondences of the underlying image data. It is noted that FIG. 4 shows the annotation 250 being translated and rotated and deformed compared to the annotation 200, which may be a result of the image registration also including a translational, rotational and deformation component, for example by being estimated as an affine transformation. It is further noted that the reference slide 50* may be labeled as a 'reference' slide by being an originally annotated pathology slide, e.g., by representing a reference for the transfer of the annotation 200 to one or more extraction slides.

Figure 5:
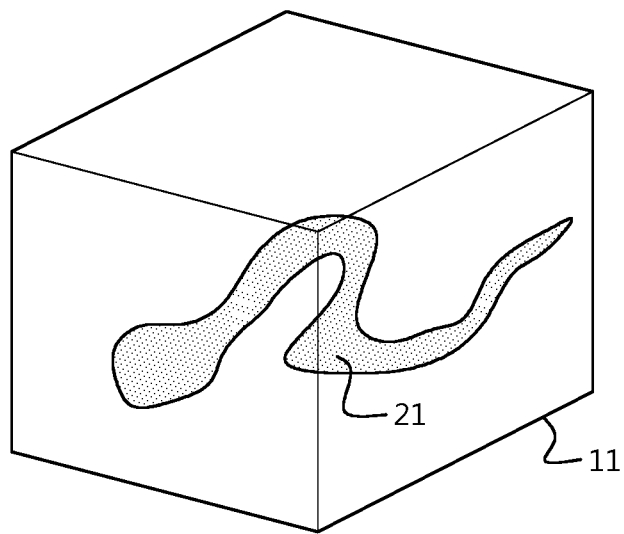
FIG. 5 shows a tissue block including a tissue strand.

FIG. 5 is similar to FIG. 1 but shows a tissue block 11 including a tissue strand and thereby tissue material 21 having a winding shape. Tissue of interest may often have such a complex shape, e.g., due to biological reasons, but also when the tissue slices are obtained from a tissue strand, such as in the case of prostate biopsy.

Figure 6:
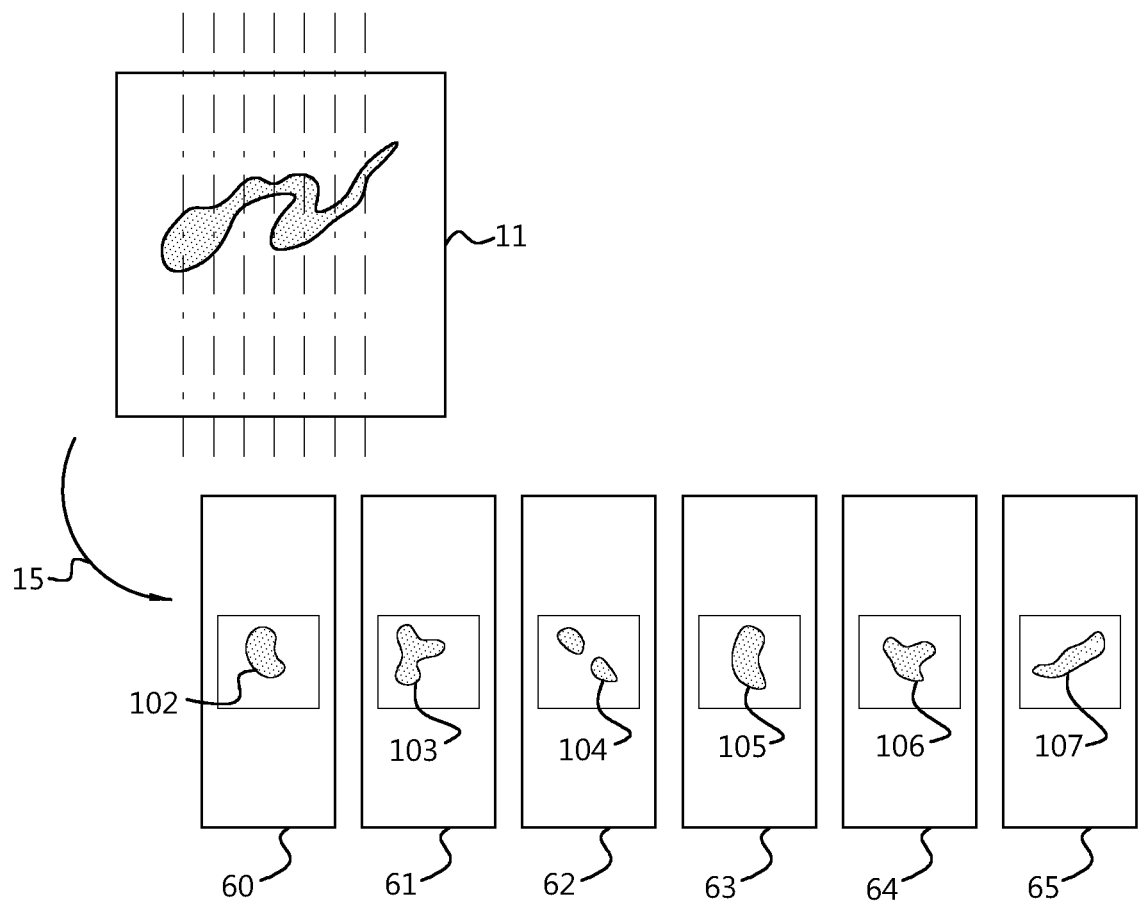
FIG. 6 illustrates the slicing of the tissue block to obtain a series of pathology slides, in which each pathology slide contains a respective tissue part.

FIG. 6 is similar to FIG. 2 in that it illustrates a slicing of the tissue block 11 and the mounting of the resulting tissue slices on glass slides. The result of the slicing and mounting on glass (both indicated by arrow 15 in FIG. 6) is a series of pathology slides 60-65 which may each contain a respective tissue part 102-107. It can be seen that when comparing FIG. 6 with FIG. 2, that the winding shape of the tissue causes the tissue parts 102-107 to have a greatly varying appearance in each of the pathology slides 60-65, e.g., having a different shape. As a result, the image registration between the pathology slides may be suboptimal, e.g., resulting in erroneous correspondences. This problem may be aggravated when the tissue of interest lies in a homogenous tissue area. In this case, the image registration may neither be guided by the tissue of interest itself, e.g., due to its varying shape, but also not by the surrounding tissue area as a lack of spatial detail does not allow the image registration to determine correspondences in the surrounding tissue area.

Accordingly, if one of the pathology slides were to contain H&E stained tissue and were to be annotated, and thereby effectively represent a reference slide, the transfer of the annotation to extraction slides may also be sub-optimal, in that it may result in the transferred annotation not matching the tissue of interest in the extraction slide. As such, the subsequent tissue dissection based on the annotation may be sub-optimal, in that insufficient tissue of interest may be extracted, or too much tissue which is not of interest.

Figure 7:
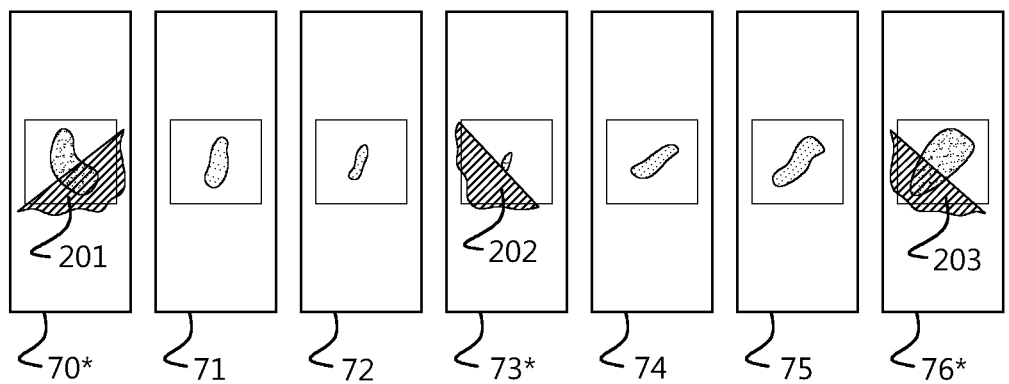
FIG. 7 illustrates the annotation of several H&E stained pathology slides to act as reference slides in the transfer of annotations to one or more extraction slides, being pathology slides positioned in between two reference slides and not being stained by H&E.

FIG. 7 illustrates the annotation of multiple H&E stained pathology slides in accordance with some embodiments of the presently disclosed subject matter. Here, a series of pathology slides 70*-76* is shown in which slides 70*, 73* and 76* are H&E stained pathology slides and which contain respective annotations 201-203, and may thereby represent reference slides. Such annotations may be already provided by a user, or as explained with reference to FIG. 9, a system may prompt the user to provide the annotations on select slides, which may already be H&E stained or may still have to be H&E stained, or use a (semi)automatic algorithm to determine the annotations on select H&E stained slides. Having obtained annotations for reference slides which are spaced apart in the series of pathology slides 70*-76* by respective sub-series of intermediate slides (e.g., slides 71 and 72, and slides 74 and 75), these annotations may be transferred to the intermediate slides in a manner as illustrated in FIG. 8 as to enable a region for tissue extraction to be identified in each of the slides.

With further reference to FIG. 7, it is noted that the transfer of the annotation may involve at least two reference slides, such as the outer slides 70* and 76*, optionally extended with one or more in-between reference slides as represented by slide 73* in FIG. 7.

Figure 8:
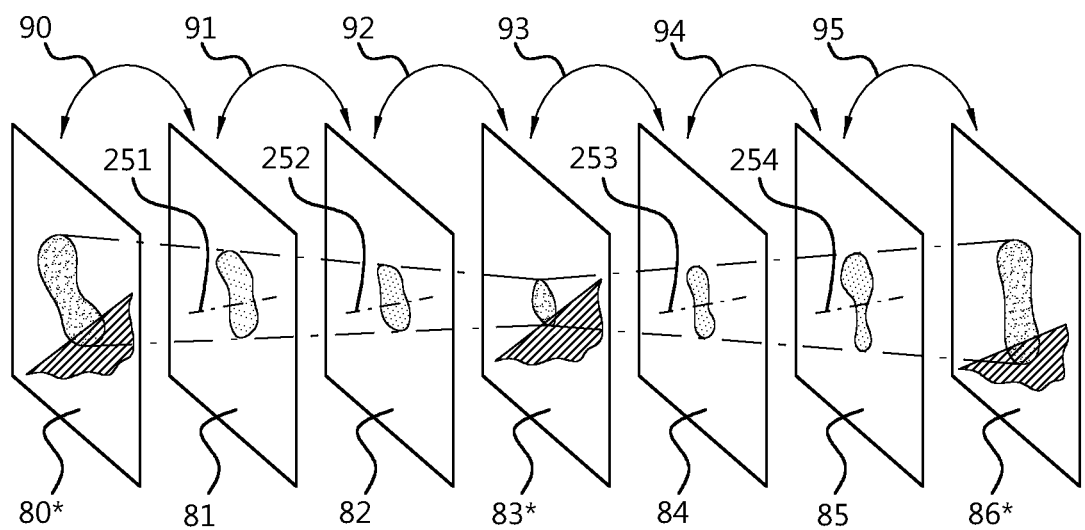
FIG. 8 illustrates the transfer of the annotations from the multiple H&E stained pathology slides to the intermediate pathology slides which are not stained by H&E.

FIG. 8 illustrates the transfer of the annotations from reference slides 80*, 83* and 86* to the extraction slides 81, 82, 84 and 85. As elsewhere, reference is made to the slides but this is understood to apply here to the digitized versions of the slides, i.e., the corresponding images. The transfers may involve the following steps, which may be applied separately (e.g., in parallel or sequentially) to each of the sub-series of intermediate slides. For example, for the first sub-series of intermediate slides 81, 82, annotations 251, 252 may be generated for the respective slides by registering each intermediate slide 81, 82 with each of the two nearest reference slides, being the first reference slide 80* and the second reference slide 83*. This 'bidirectional' registration may involve a direct registration between the respective slides, e.g., between the first reference slide 80* and the intermediate slide 81 and between the second reference slide 83* and the intermediate slide 81. Alternatively, as is also shown in FIG. 8, the registration of an intermediate slide with each of the reference slides may take place via a chain of registrations. For that purpose, each consecutive pair of slides may be mutually registered, as is shown in FIG. 8 by reference numerals 90-95 each representing a registration between a respective pair of slides. A registration between a reference slide and a respective intermediate slide may then be obtained as a superposition of the individual registrations. For example, the intermediate slide 81 may be registered with the first reference slide 80* via registration 90, and with the second reference slide 83* with the superposition of registration 91 and registration 92. The registration, either direct or via a chain, may then yield for each intermediate slide 81, 82 a first set of registration parameters representing an at least partial registration of the intermediate slide 81, 82 with the first reference slide 80* and a second set of registration parameters representing an at least partial registration of the intermediate slide 81, 82 with the second reference slide 83*.

The annotations in both reference slides 80*, 83* may then be propagated and thereby transferred to the intermediate slide 81, 82 in a manner as described elsewhere, which is also schematically shown in FIG. 8 by dashed lines, and subsequently combined to obtain combined annotations 251, 252 in the respective intermediate slides 81, 82. The above process may also be performed for the second sub-series of intermediate slides 84, 85 in substantially the same manner, except for now using as the two nearest reference slides the second reference slide 83\* and the third reference slide 86\*, resulting in combined annotations 253, 254 for the intermediate slides 84, 85.

In general, the annotations may be transferred in the above described manner by H&E staining the tissue of at least two pathology slides. In a series of pathology slides, these may be the first slide and the last slide, or in general any two slides which are spaced apart by a series of intermediate slides which represent extraction slides. After digitization, the H&E stained slides may be annotated to identify a region for tissue dissection, and thereby become reference slides for the intermediate extraction slides. The annotations in both reference slides may then be transferred to each or at least one of the intermediate extraction slides, which may involve bidirectional registration, e.g., from the intermediate slide 'forward' to one of the reference slides and 'backward' to the other reference slide. Such bidirectional registration may involve performing a known image registration twice, and may for example be based on feature-based image registration, image registration using an active contour model, image registration using shape context or image registration using the level set method. Having obtained the forward and back registrations, each annotation may then be propagated to the intermediate slide by adjusting the shape and/or position of the annotation in correspondence with the underlying image data, thereby obtaining a 'forward annotation' and a 'backward annotation', with the adjectives 'forward' and 'backward' referring here to the origin of the respective annotation within the series of pathology slides, e.g., earlier or later in the series. Both annotations may then be combined, for example based on techniques such as distance transform, shape context or by morphological operations, for example by using an overlap between the two annotations. A specific example may be that both annotations may be combined as a logical 'AND', i.e., the intersection of both annotations, or as a logical 'OR', i.e., the union of both annotations.

Another specific example is that a signed distance transform may be applied to each transferred annotation to obtain two signed distance-transformed images. Both signed distance-transform images may then be added together, and the combined annotation region may be determined as the region where the added pixel values are positive.

If both annotations are too different, e.g., in terms of shape, it may be advised by the system generating the annotation (e.g., the system of FIG. 9) to stain an intermediate slide with H&E and to annotate the slide. This slide may then be used as a reference slide, thereby reducing the average distance between reference slides in the series of pathology slides and thereby reducing the likelihood that both annotations are too different. In general, a quality of fit measure may be used to assess a difference between the annotations and/or between the image data to determine whether it is needed to stain and annotate an intermediate slide. A specific example is that the quality of fit may be expressed as the magnitude of a deformation of the propagated first annotation and/or of the propagated second annotation, for example as the magnitude of a non-rigid component of a transformation defined by a set of transformation parameters. Additionally or alternatively, the quality of fit may be expressed as a difference in shape, or overlap in surface area, of the propagated first annotation and the propagated second annotation. The difference in shape may for example be quantified by a difference in the contour of the annotation.

The techniques as described with reference to FIG. 8 and others may be implemented by an appropriately configured system or a computer-implemented method.

Figure 9:
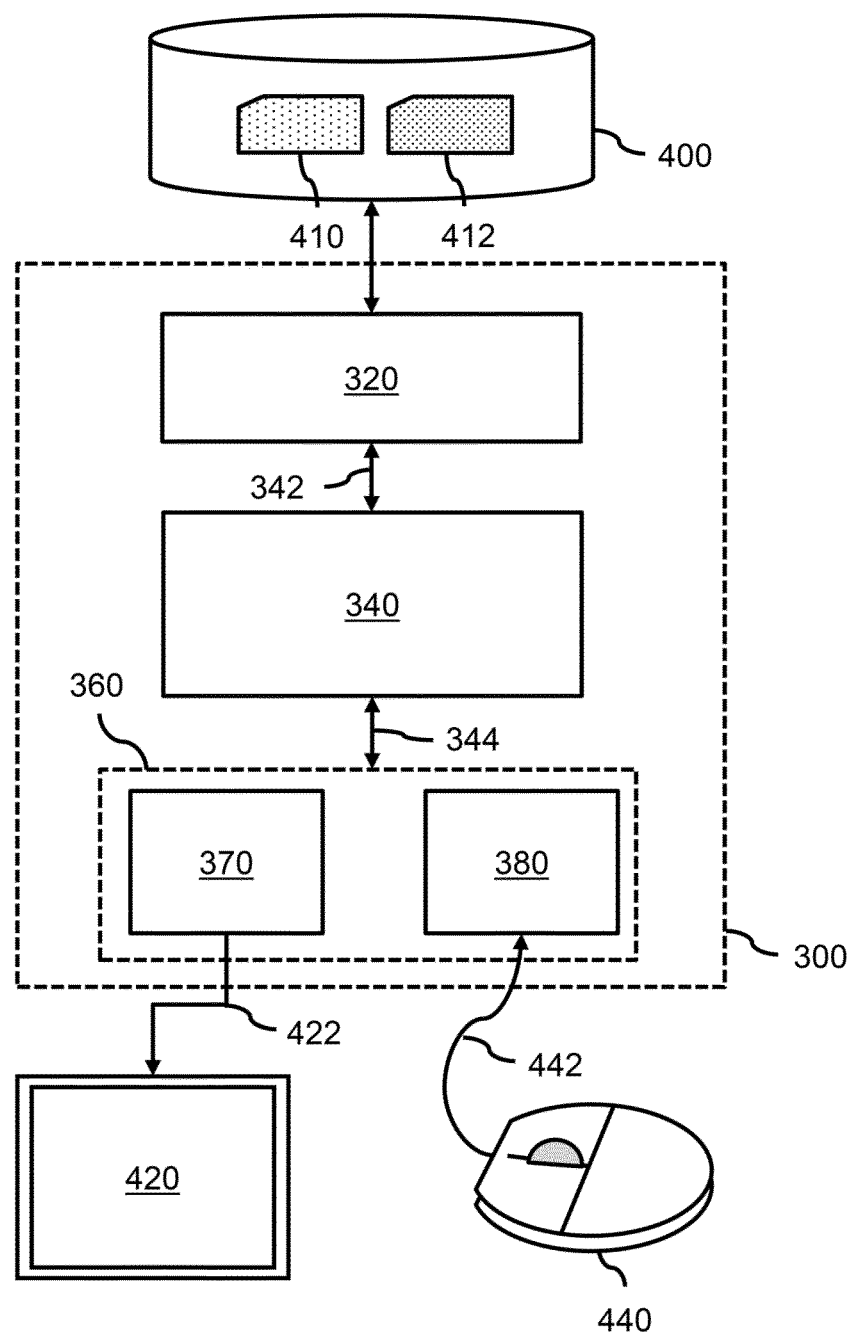
FIG. 9 shows a system for determining tissue dissection regions.

FIG. 9 shows a system 300 for determining one or more regions for tissue dissection in a series of pathology slides using a series of images which represent a digitized version of the series of pathology slides. The system 300 includes a data interface 320 configured to access image data 410 of the series of images. In the example of FIG. 9, the data interface 320 is shown to be connected to an external data storage 400 which includes the image data 410. The data storage 400 may, for example be constituted by, or be part of, a Picture Archiving and Communication System (PACS) of a Hospital Information System (HIS) to which the system 300 may be connected or included in, or may be any other type of data storage, such as a hard drive, SSD, or an array thereof. Accordingly, the system 300 may obtain access to the image data 410 via external data communication. Alternatively, the image data 410 may be accessed from an internal data storage of the system 300 (not shown). In general, the data interface 320 may take various forms, such as a network interface to a Local Area Network (LAN) or a Wide Area Network (WAN), such as the Internet, a storage interface to an internal or external data storage, etc.

The system 300 is further shown to include a processor subsystem 340 configured to internally communicate with the data interface 320 via data communication 342. The processor subsystem 340 is further shown to internally communicate with a user interface subsystem 360 via data communication 344. The user interface subsystem 360 may be configured to, during operation of the system 300, enable a user to interact with the system 300, for example using a graphical user interface. The user interface subsystem 360 is shown to include a user input interface 380 configured to receive user input data 442 from a user input device 440 operable by the user. The user input device 440 may take various forms, including but not limited to a computer mouse, touch screen, keyboard, microphone, etc. FIG. 9 shows the user input device to be a computer mouse 080. In general, the user input interface 380 may be of a type which corresponds to the type of user input device 440, i.e., it may be a thereto corresponding type of user device interface 380.

The user interface subsystem 360 is further shown to include a display output interface 370 configured to provide display data 422 to a display 420 to visualize output of the system 300. In the example of FIG. 9, the display is an external display 420. Alternatively, the display may be an internal display. It is noted that instead of a display output interface 370, the user interface subsystem 360 may also include another type of output interface which is configured to render output data in a sensory-perceptible manner to the user.

The processor subsystem 340 may be configured to, during operation of the system 300 and using the user interface subsystem 360, establish a user interface which enables the user to annotate the image data, and in particular, to provide a first annotation identifying a first region for tissue dissection in a first image of the series of images and to provide a second annotation identifying a second region for tissue dissection in a second image of the series of images, wherein the first image and the second image are separated in the series of images by a series of intermediate images. It is noted that in some embodiments, the first and second annotations may be obtained (semi)automatically by the processor subsystem 340. In this case, the role of the user changes and the user data (input and output, 442 and 422) may be adapted to that different role. In general, the manual, semi-automatic or automatic annotation may result in annotation input data which defines the first annotation and the second annotation in a computer-readable manner, which data may be accessed by the processor subsystem 340 via a further data interface (not separately shown in FIG. 9) which may for example be a memory interface of the processor subsystem, or in case the annotation input data is stored in the data storage 400, the same or same type of data interface as the data interface 320. The processor subsystem 340 may be further configured to generate an annotation for one or more intermediate images from the series of intermediate images in a manner as described elsewhere, e.g., with reference to FIGS. 8 and 10. As a result thereof, annotation output data 412 may be obtained which may be stored in the data storage 400 and/or used by a tissue dissection system.

Although not shown in FIG. 9, in some embodiments, the system 300 may include an interface to a tissue dissection system so as to control the tissue dissection system to dissect tissue from one or more pathology slides which correspond to the one or more intermediate images based on the one or more annotations generated for the one or more intermediate images. In other embodiments, the system 300 may be part of such a tissue dissection system, e.g., in the form of a subsystem thereof. Furthermore, in some embodiments, the processor subsystem 340 may be configured to determining a quality of fit of the annotation in the intermediate image, and if the quality of fit does not satisfy a quality of fit criterion, alerting a user to provide a third annotation in a third image which is included in the series of intermediate images between the first image and the second image. For example, the processor subsystem 340 may via the user interface subsystem 360 generate an onscreen warning for display by the display 420. In some embodiments, the processor subsystem 340 may also indicate, via the user interface subsystem 360, a recommended location of the third image within the series of images, e.g., as an onscreen message specifying the location or by highlighting a visual representation of the particular slide on the display 420. In general, the processor subsystem 340 may provide, via the user interface subsystem 360, instructions to the user that are to be executed in order to provide the third annotation using the third reference image of an intermediate third reference slide. In some embodiments, once a newly stained slide is again digitized, the processor subsystem 340 may, via the user interface subsystem 360, prompt the user to annotate the slide. Having obtained the annotation, the processor subsystem 340 may then then proceed with using the newly stained slide as a reference slide to generate annotations for extraction slides.

In general, the system 300 may be embodied as, or in, a single device or apparatus, such as a workstation or pathology system, e.g., a tissue dissection system or a pathology system which interfaces with such a tissue dissection system. The device or apparatus may include one or more microprocessors, e.g., CPUs and/or GPUs, which together may represent the processor subsystem and which may execute appropriate software. The software may have been downloaded and/or stored in a corresponding memory, e.g., a volatile memory such as RAM or a non-volatile memory such as Flash. Alternatively, the functional units of the system, e.g., the data interface, the user input interface, the display output interface and the processor subsystem, may be implemented in the device or apparatus in the form of programmable logic, e.g., as a Field-Programmable Gate Array (FPGA). In general, each functional unit of the system may be implemented in the form of a circuit. It is noted that the system 300 may also be implemented in a distributed manner, e.g., involving different devices or apparatuses. For example, the distribution may be in accordance with a client-server model, e.g., using a server and a thin-client. For example, computationally complex operations such as the image registration and the propagation of the annotations may be performed by one or more servers, e.g., one or more cloud-based server(s) or a high-performance computing system, while the annotation may be generated at the client, e.g., by the user, who may operate a user input device which is connected to the client. In such examples, the processor subsystem of the system 300 may be represented by the microprocessors of the distributed servers and/or clients.

Figure 10:
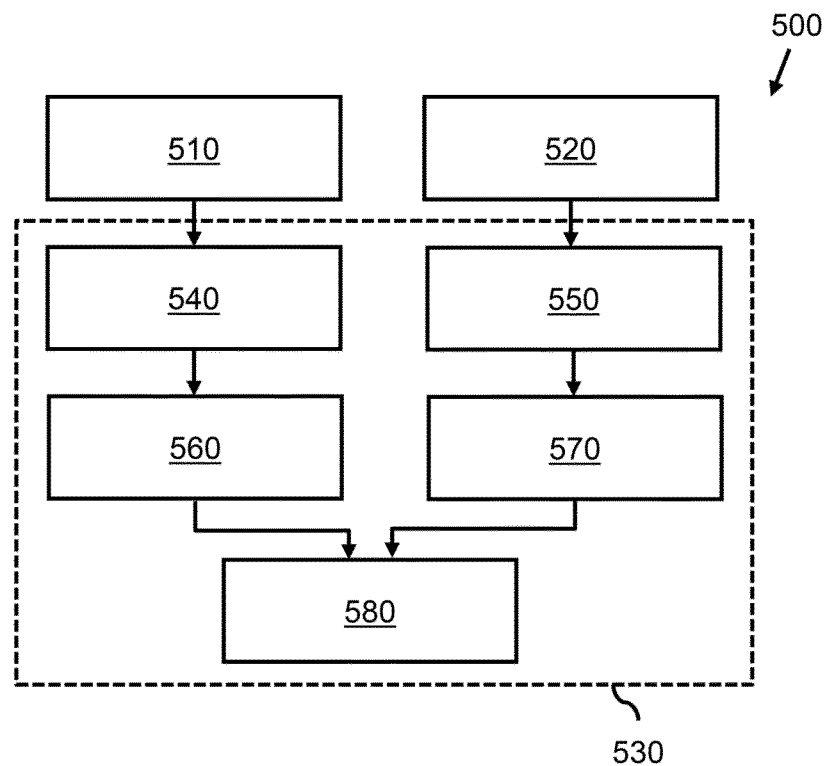
FIG. 10 shows a method for determining tissue dissection regions.

FIG. 10 shows a method 500 for determining one or more regions for tissue dissection in a series of pathology slides using a series of images which represent a digitized version of the series of pathology slides. The method 500 is shown to include, in a step titled 'OBTAINING FIRST ANNOTATION IN FIRST IMAGE', obtaining 510 a first annotation identifying a first region for tissue dissection in a first image of the series of images. The method 500 is further shown to include, in a step titled 'OBTAINING SECOND ANNOTATION IN SECOND IMAGE', obtaining 520 a second annotation identifying a second region for tissue dissection in a second image of the series of images, wherein the first image and the second image are separated in the series of images by a series of intermediate images. The method 500 is further shown to include, in a step titled 'GENERATING ANNOTATION FOR INTERMEDIATE IMAGE(S)', generating 530 an annotation for one or more intermediate images from the series of intermediate images by, for each one of the one or more images, performing the following steps 540-580. Namely, the step 530 is shown to include, in a step titled 'DETERMINING FIRST SET OF REGISTRATION PARAMETERS', determining 540 a first set of registration parameters representing an at least partial registration of the intermediate image with the first image. The step 530 is further shown to include, in a step titled 'DETERMINING SECOND SET OF REGISTRATION PARAMETERS', determining 550 a second set of registration parameters representing an at least partial registration of the intermediate image with the second image. The step 530 is further shown to include, in a step titled 'PROPAGATING FIRST ANNOTATION TO INTERMEDIATE IMAGE', propagating 560 the first annotation from the first image to the intermediate image using the first set of registration parameters. The step 530 is further shown to include, in a step titled 'PROPAGATING SECOND ANNOTATION TO INTERMEDIATE IMAGE', propagating 570 the second annotation from the second image to the intermediate image using the second set of registration parameters. The step 530 is further shown to include, in a step titled 'COMBINING PROPAGATED FIRST ANNOTATION AND SECOND ANNOTATION', combining 580 the propagated first annotation and second annotation to obtain the annotation in the intermediate image.

Figure 11:
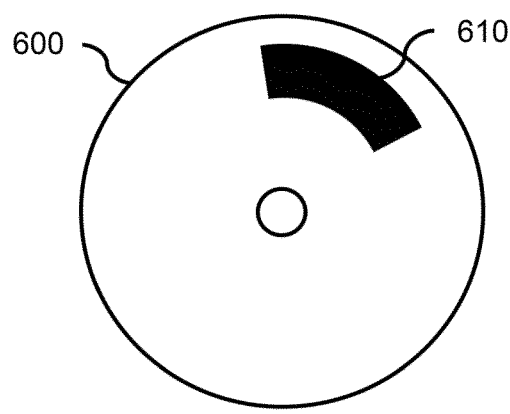
FIG. 11 shows a computer-readable medium including non-transitory data.

It will be appreciated that, in general, the steps of the method 500 of FIG. 10 may be performed in any suitable order, e.g., consecutively, simultaneously, or a combination thereof, subject to, where applicable, a particular order being necessitated, e.g., by input/output relations. The method 500 may be implemented on a computer as a computer implemented method, as dedicated hardware, or as a combination of both. As also illustrated in FIG. 11, instructions for the computer, e.g., executable code, may be stored on a computer readable medium 600, e.g., in the form of a series 610 of machine-readable physical marks and/or as a series of elements having different electrical, e.g., magnetic, or optical properties or values. The executable code may be stored in a transitory or non-transitory manner. Examples of computer readable mediums include memory devices, optical storage devices, cloud storage devices, etc. FIG. 11 shows an optical disc 600.

It should be noted that the above-mentioned embodiments illustrate rather than limit some embodiments of the presently disclosed subject matter, and that those or ordinary skill in the art will be able to design many alternative embodiments. In the claims, any reference signs placed between parentheses shall not be construed as limiting the claim. Use of the verb "include" and its conjugations does not exclude the presence of elements or steps other than those stated in a claim. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. Some embodiments of the presently disclosed subject matter may be implemented by hardware including several distinct elements, and by a suitably programmed computer. In the device claim enumerating several distinct elements, several of these elements may be embodied by one and the same item of hardware. The mere fact that certain measures are recited in mutually different dependent claims does not indicate that a combination of these measures cannot be used to advantage.

The invention claimed is:

1. A computer-implemented method for determining one or more regions for tissue dissection in a series of pathology slides using a series of images which represent a digitized version of the series of pathology slides, the method comprising:
   obtaining a first annotation identifying a first region for tissue dissection in a first image of the series of images;
   obtaining a second annotation identifying a second region for tissue dissection in a second image of the series of images, wherein the first image and the second image are separated in the series of images by a series of intermediate images; and
   generating an annotation for one or more intermediate images from the series of intermediate images by, for each one of said one or more images:
      determining a first set of registration parameters representing an at least partial registration of the intermediate image with the first image;
      determining a second set of registration parameters representing an at least partial registration of the intermediate image with the second image;
      propagating the first annotation from the first image to the intermediate image using the first set of registration parameters;
      propagating the second annotation from the second image to the intermediate image using the second set of registration parameters; and
      combining said propagated first annotation and second annotation to obtain the annotation in the intermediate image.

2. The method according to claim 1, wherein:
   the first set of registration parameters and the second set of registration parameters each define a deformable registration; and
   propagating the first annotation to the intermediate image and propagating the second annotation to the intermediate image each comprise deforming the respective annotation based on the respective set of registration parameters.

3. The method according to claim 2, further comprising:
   determining a quality of fit of the annotation in the intermediate image by determining a magnitude of a deformation of the propagated first annotation and/or of the propagated second annotation; and
   if the quality of fit does not satisfy a quality of fit criterion, alerting a user to provide a third annotation in a third image which is comprised in the series of intermediate images between the first image and the second image.

4. The method according to claim 1, further comprising:
   determining a quality of fit of the annotation in the intermediate image; and
   if the quality of fit does not satisfy a quality of fit criterion, alerting a user to provide a third annotation in a third image which is comprised in the series of intermediate images between the first image and the second image.

5. The method according to claim 4, wherein alerting the user comprises indicating a location of the third image within the series of intermediate images or a location of a corresponding pathology slide within the series of pathology slides.

6. The method according to claim 5, wherein:
   determining the quality of fit of the annotation in the intermediate image comprises determining a first quality of fit of the propagated first annotation and a second quality of fit of the propagated second annotation; and
   the method further comprises determining the location of the third image based on a comparison of the first quality of fit and the second quality of fit.

7. The method according to claim 4, wherein:
   the first image and the third image are separated in the series of images by a first subseries of intermediate images;
   the second image and the third image are separated in the series of images by a second subseries of intermediate images; and
   wherein the method further comprises:
   generating an annotation for one or more intermediate images of the first subseries of intermediate images based on the first annotation and the third annotation; and
   generating an annotation for one or more intermediate images of the second subseries of intermediate images based on the second annotation and the third annotation.

8. The method according to claim 4, wherein determining the quality of fit comprises determining a difference in shape, or overlap in surface area, of the propagated first annotation and the propagated second annotation.

9. The method according to claim 1, wherein the first set of registration parameters and the second set of registration parameters are determined by one of the group of:
   feature-based image registration;
   image registration using an active contour model;
   image registration using shape context; and
   image registration using the level set method.

10. The method according to claim 1, wherein the first image and the second image are of Hematoxylin and Eosin (H&E) stained pathology slides.

11. The method according to claim 1, wherein the series of intermediate images are of pathology slides which are unstained in paraffin, unstained without paraffin and/or stained with Nuclear Fast Red (NFR).

12. The method according to claim 1, further comprising controlling a tissue dissection system to dissect tissue from one or more pathology slides which correspond to the one or more intermediate images based on the one or more annotations generated for the one or more intermediate images.

13. A non-transitory computer-readable medium comprising data representing instructions arranged to cause a processor system to perform the computer-implemented method according to claim 1.

14. A system for determining one or more regions for tissue dissection in a series of pathology slides using a series of images which represent a digitized version of the series of pathology slides, the system comprising:
  a data interface for accessing the series of images;
  a further data interface for accessing annotation input data defining:
    a first annotation identifying a first region for tissue dissection in a first image of the series of images, and
    a second annotation identifying a second region for tissue dissection in a second image of the series of images, wherein the first image and the second image are separated in the series of images by a series of intermediate images; and
  a processor subsystem configured to:
    generate an annotation for one or more intermediate images from the series of intermediate images by, for each one of said one or more images:
      determining a first set of registration parameters representing an at least partial registration of the intermediate image with the first image;
      determining a second set of registration parameters representing an at least partial registration of the intermediate image with the second image;
      propagating the first annotation from the first image to the intermediate image using the first set of registration parameters;
      propagating the second annotation from the second image to the intermediate image using the second set of registration parameters; and
      combining said propagated first annotation and second annotation to obtain the annotation in the intermediate image.

15. The system according to claim 14, wherein the system is part of or configured to interface with a tissue dissection system.

* * * * *